United States Patent
Melching et al.

(10) Patent No.: US 7,013,197 B2
(45) Date of Patent: Mar. 14, 2006

(54) CLIMATIC CABINET AND DEVICE AND METHOD FOR ITS MONITORING

(75) Inventors: Achim Melching, Langenselbold (DE); Heiko Reinhardt, Hanau (DE); Thorsten Dick, Fulda (DE); Stefan Betz, Erlensee (DE)

(73) Assignee: Kendro Laboratory Products GmbH, Langenselbold (DE)

( * ) Notice: Subject to any disclaimer, the term of this patent is extended or adjusted under 35 U.S.C. 154(b) by 54 days.

(21) Appl. No.: 10/766,901

(22) Filed: Jan. 30, 2004

(65) Prior Publication Data

US 2004/0212285 A1    Oct. 28, 2004

(30) Foreign Application Priority Data

Feb. 2, 2003    (DE) ................................ 103 04 171

(51) Int. Cl.
   *G06F 7/00*    (2006.01)
(52) U.S. Cl. ........................................ 700/213; 422/119
(58) Field of Classification Search ................ 700/213, 700/242, 244; 422/119, 55, 63, 65
   See application file for complete search history.

(56) References Cited

U.S. PATENT DOCUMENTS

| | | | | |
|---|---|---|---|---|
| 4,676,951 A | * | 6/1987 | Armes et al. ................ | 422/65 |
| 5,233,844 A | * | 8/1993 | Knippscheer et al. ......... | 62/440 |
| 6,673,595 B1 | * | 1/2004 | Barbera-Guillem ...... | 435/286.2 |
| 6,941,762 B1 | * | 9/2005 | Felder et al. .................. | 62/63 |

FOREIGN PATENT DOCUMENTS

EP    1 155 743 A2    11/2001

(Continued)

OTHER PUBLICATIONS

European Search Report dated Jun. 7, 2004 XP002283549; Derwent Publications Ltd., London Database WPI Week 199612; Jan. 16, 1996; 1 page.

*Primary Examiner*—Khoi H. Tran
(74) *Attorney, Agent, or Firm*—Baker & Hostetler LLP

(57) ABSTRACT

The invention concerns a climatic cabinet with specimen storage places and a transporting device and a monitoring device for specimen slides. The invention also concerns a device and a method for the monitoring of a climatic cabinet. The monitoring device is designed, with respect to its form and outside dimensions, so that it can be transported by the transporting system and can be laid on one of the specimen storage places and can be removed from a specimen storage place.

That has the advantage that the monitoring device can be moved to any place with the already present transporting device, wherein not only individual specimen slides but also specimen slide cassettes can be taken to their storage places and monitored, as well as stationary and movable storage devices in a position at rest and in operation, such as cassette carrier carousels, and parts of the transporting device itself. Another advantage is to be found in the fact that the filling of the climatic cabinet can take place by means of specimen slide cassettes, instead of an individual filling, and subsequently, a simple identification of the introduced specimen slides can take place.

A preferred further refinement of the invention consists in a specimen storage place for the storage of the monitoring device being affixed to the outside of the climatic cabinet, which increases the service life and functioning reliability, since the monitoring device is not constantly exposed to the climate in the climatic cabinet, and furthermore, facilitates maintenance.

12 Claims, 1 Drawing Sheet

FOREIGN PATENT DOCUMENTS

| | | |
|---|---|---|
| FR | 2 820 144 | 8/2002 |
| JP | 57189901 | 11/1982 |
| JP | 2000241067 | 9/2000 |
| JP | 2001122410 | 5/2001 |

* cited by examiner

CLIMATIC CABINET AND DEVICE AND METHOD FOR ITS MONITORING

FIELD OF THE INVENTION

The invention concerns a climatic cabinet with specimen storage places and a transporting device and a monitoring device for specimen slides he invention also concerns a device and a method for the monitoring of a climatic cabinet.

BACKGROUND OF THE INVENTION

Such a climatic cabinet is known from EP-A2-1155743. A common use is the occasional storage of specimen slides, typically, so-called microtiter plates (MTP), under prespecified climatic conditions, for research purposes and use in industrial manufacturing. The loading and unloading of specimen slides takes place individually via a small transfer opening with the aid of an automatic transporting device. The specimen slide is hereby grasped with a blade or a gripper and transported from and to the individual specimen slide storage places by means of a lift and an arm which swivels horizontally.

For specimen slides with a barcode marking, the providing of a monitoring device in the form of a barcode reader in the area of the transfer opening is also known, wherein, however, only passing specimen slides can be identified. However, if a specimen slide, which has already been laid on a storage place, is to be examined, that is not readily possible. Such climatic cabinets are provided with a relatively large door, through which ample access to the interior is possible. For obvious reasons, however, they may not be opened during the operation of the climatic cabinet.

SUMMARY OF THE INVENTION

The problem of the invention is to devise a climatic cabinet and a device and a method of the type mentioned in the beginning, with which a monitoring can be simply undertaken in the interior of the climatic cabinet.

This problem is solved, in accordance with the invention, in that the monitoring device is designed, with regard to its shape and outside dimensions, in such a way that it can be transported by the transporting system and can be laid on one of the specimen storage places and removed from a specimen storage place.

A basic thought of the invention is to design the monitoring device compatible with a specimen slide, so that it can be handled and transported like a specimen slide, with the means already present and installed. This has the advantage that they are moved to a site with the already present transporting device and can be swiveled into different horizontal angle positions. With it, not only can individual specimen slides be taken to their storage places and monitored, but also specimen slide cassettes, stationary and movable storage devices in a position at rest and in operation, such as cassette carrier carousels, and not least, parts of the transporting device itself. Another advantage is to be found in that the filling of the climatic cabinet by means of specimen slide cassettes can be undertaken, instead of an individual filling, and subsequently, a simple identification of the introduced specimen slide can be carried out.

A preferred further refinement of the invention consists in affixing a specimen storage place for the storage of the monitoring device outside the climatic cabinet. Thus, the monitoring device is not constantly exposed to the climate in the climatic cabinet, which increases the service life and functioning reliability. Furthermore, the maintenance is facilitated.

It is particularly expedient for a wireless data transmission path for the monitoring device to be present, and that it be preferably designed for radio transmission or infrared transmission. According to one preferred development of the invention, the monitoring device also has moreover a sender and/or a receiver.

For operation with wireless transmission, it is also advantageous for the specimen storage place provided for the storage of the monitoring device, to have a stationary data transmission interface and/or a storage battery-loading station, and that the monitoring device be provided with counterparts of these interfaces and with a data storage unit for the intermediate storage of the determined data.

As a function of the identifications and monitorings to be carried out, it is expedient for the monitoring device, as a detector, to have a barcode reader, a photographic camera, or an inductive sensor. With a photographic camera, for example, it is also possible to examine empty specimen storage places or to identify specimen slides with incomplete or missing barcodes.

In accordance with the method, the problem is solved in that the monitoring device is laid on a specimen storage place in a resting mode, that it is taken from the specimen storage place by the transporting device in an operating mode and is moved to the site to be monitored, and that it subsequently is laid on a specimen storage place by the transporting device.

A particularly reliable operation is attained in that the specimen storage place, equipped with a stationary data transmission interface and/or storage battery-loading station, is used for the resting mode.

A time and path optimization of the transporting device can be attained in that the monitoring device is placed for intermediate storage on a free specimen storage place which is closest at the time. That has the advantage that the transporting of specimen slides can be carried out with the shortest possible interruptions.

BRIEF DESCRIPTION OF THE DRAWING

The invention will be further explained below, with the aid of an embodiment example shown in the drawing.

The single FIGURE schematically shows a partial longitudinal section through a climatic cabinet.

DETAILED DESCRIPTION OF THE INVENTION

Figure 1:
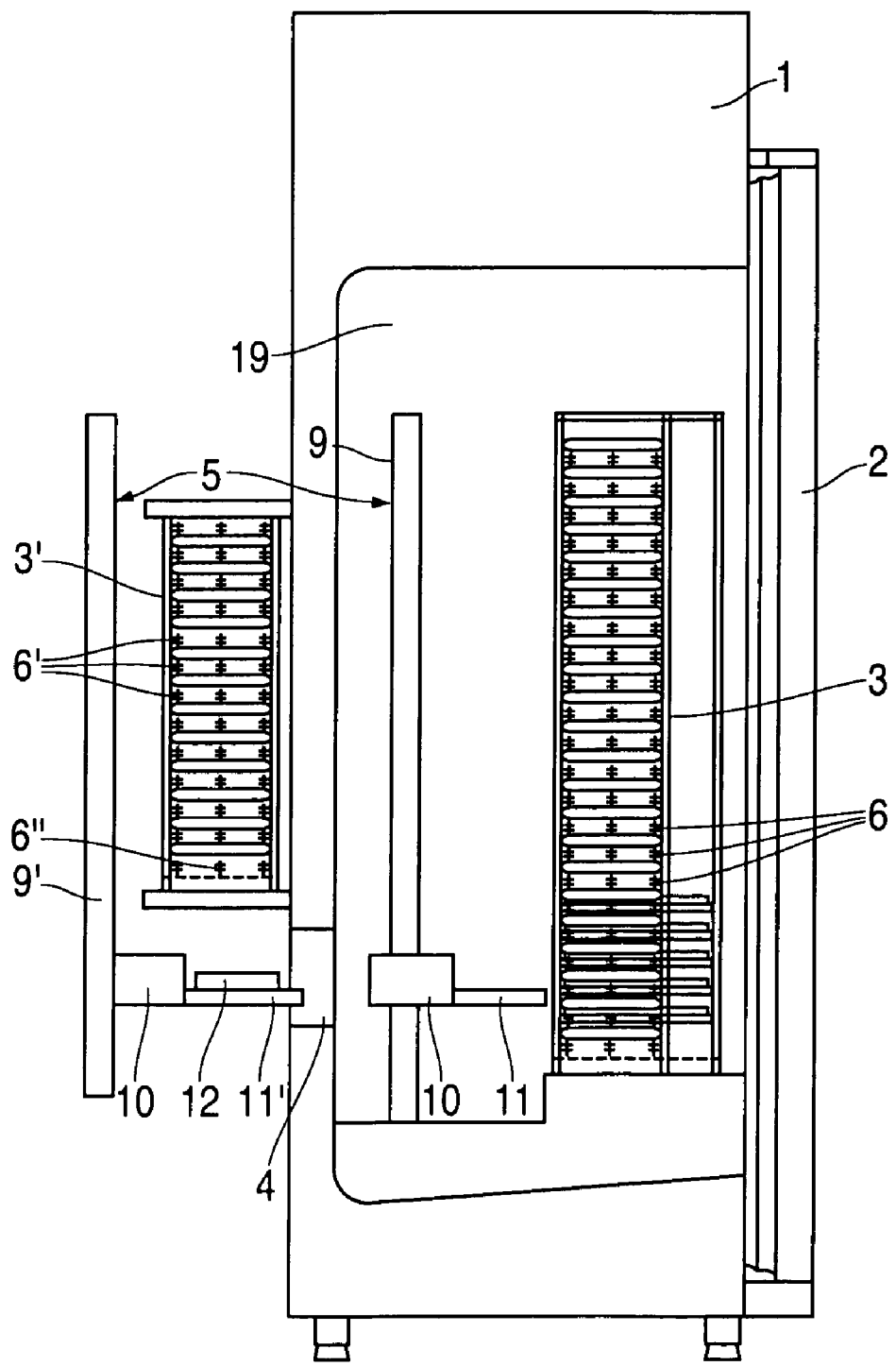

The climatic cabinet 1, illustrated in the FIGURE, has a spacious service door 2 to a usable space 19, through which specimen storage stations 3 can be mounted and removed and through which maintenance operations, and the like, are possible. In the opposite wall of the climatic cabinet 1, a transfer opening 4 is present, through which, by means of a transporting device 5, specimen slides can be introduced into the climatic cabinet 1 and into the specimen storage stations 3 and can be removed from them. Each specimen storage station comprises a large number of specimen storage places 6.

Another external specimen storage station 3' with additional specimen storage places 6' is affixed on an outer side of the climatic cabinet. There is a transporting connection between the external specimen storage places 6' of the external specimen storage station 3' and the internal specimen storage places 6 of the internal specimen storage stations 3.

The transporting device 5 comprises an external part 7 and an internal part 8 respectively with a lift 9, 9' and with a horizontal sliding unit 10, 10', located on it, and a gripper or a blade 11, 11'. The blades 11, 11' take up a specimen slide during removal from a specimen storage place 6, 6' and carry it, during transport, to and from the specimen storage places 6, 6'. A loading from one blade 11 to another 11' during the transfer from the inner and outer parts 7, 8 of the transporting device 5 takes place with a transfer device, which is not depicted.

In the depicted situation, the blade 11' carries a monitoring device 12, which is designed, with regard to its shape and outside dimensions, in such a way that compatible with a specimen slide, it can be transported by the transporting device 5 and laid on one of the specimen storage places 6, 6' and can be removed from a specimen storage place 6, 6'. As a sensor, the monitoring device 12 is equipped, for example, with a barcode reader, a photographic camera, or an inductive sensor (not depicted). With the transporting device 5, the monitoring device 12 can be moved, in the same way as a common specimen slide to any specimen storage place 6, 6', in order to examine the site or the specimen storage station 3, and the like. Measurement and control signals are transmitted wireless to a receiver (not depicted). Alternately or additionally, measurement data can also be recorded in a data storage of the monitoring device and read at a stationary interface.

A selected specimen storage place 6" of the external specimen storage station 3' is set up as a storage place for the monitoring device 12 in a resting mode. It has the data transmitting interface and a storage battery-loading station (not depicted) for the monitoring device 12. After ending a monitoring operation, the transporting device 5 lays the monitoring device 12 on this selected specimen storage place 6". If it is expedient for the time and path optimization, the monitoring device 12 can be placed, for temporary intermediate storage, on any free specimen storage place 6, 6', when one of the specimen slides has to be transported.

A not depicted control unit relates all identification features of the specimen slides with the individual specimen storage places 6, 6', 6", coordinates the transporting path and the individual position of the transporting device 5, and carries out the classification and evaluation of the examination results, etc.

What is claimed is:

1. Climatic cabinet with specimen storage places and a transporting device and a monitoring device for specimen slides, characterized in that the monitoring device is so designed, with regard to its shape and outside dimensions, in such a way that it can be transported by the transporting system and laid on one of the specimen storage places and can be removed from a specimen storage place.

2. Climatic cabinet according to claim 1, characterized in that a specimen storage place for the storage of the monitoring device is affixed to the outside of the climatic cabinet.

3. Climatic cabinet according to claim 1, characterized in that the specimen storage place, provided for the storage of the monitoring device, has a stationary data transmission interface and/or a storage-battery-loading station.

4. Climatic cabinet according to claim 1, characterized in that a wireless data transmission path is present for the monitoring device.

5. Climatic cabinet according to claim 4, characterized in that the wireless data transmission path is designed for a radio transmission or an infrared transmission.

6. Monitoring device for a climatic cabinet according to claim 1, characterized in that it is designed, with regard to its shape and outside dimensions, so that it can be transported by the transporting system and laid on one of the specimen storage places and can be removed from a specimen storage place.

7. Subject matter according to claim 1, characterized in that the monitoring device has a counterpart for the stationary data transmission interface or the storage battery-loading station.

8. Subject matter according to claim 7, characterized in that the monitoring device has a sender and/or a receiver.

9. Subject matter according to claim 7, characterized in that the monitoring device has, as a detector, a barcode reader, a photographic camera, or an inductive sensor.

10. Method for the examination of a specimen in a climatic chamber according to claim 1, characterized in that the monitoring device is laid on a specimen storage place in a resting mode, that it is removed from the specimen storage place in an operating mode by the transporting device and is moved to the site to be monitored, and that it is subsequently laid on a specimen storage place by the transporting device.

11. Method according to claim 10, characterized in that the specimen storage place, equipped with stationary data transmission interface and/or battery storage-loading station, is used for the resting mode.

12. Method according to claim 10, characterized in that the monitoring device is placed, for intermediate storage, on a free specimen storage place, which is closest at the time.

* * * * *